United States Patent
Zhong et al.

(10) Patent No.: US 9,622,688 B2
(45) Date of Patent: Apr. 18, 2017

(54) LANCET-RELEASE MECHANISM

(71) Applicant: Ascensia Diabetes Care Holdings AG, Basel (CH)

(72) Inventors: Weiping Zhong, Granger, IN (US); Tieming Ruan, Randolph, NJ (US); Derek Lok, Mohegan Lake, NY (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 103 days.

(21) Appl. No.: 14/310,552

(22) Filed: Jun. 20, 2014

(65) Prior Publication Data

US 2014/0303661 A1 Oct. 9, 2014

Related U.S. Application Data

(63) Continuation of application No. 11/885,526, filed as application No. PCT/US2006/007682 on Mar. 3, 2006, now Pat. No. 8,784,444.

(Continued)

(51) Int. Cl.
*A61B 17/14* (2006.01)
*A61B 5/15* (2006.01)
*A61B 5/151* (2006.01)

(52) U.S. Cl.
CPC .......... *A61B 5/1411* (2013.01); *A61B 5/1519* (2013.01); *A61B 5/150022* (2013.01);
(Continued)

(58) Field of Classification Search
CPC .................................................... A61B 5/1411
(Continued)

(56) References Cited

U.S. PATENT DOCUMENTS 3,797,488 A 3/1974 Hurschman et al.
4,203,446 A 5/1980 Hofert et al.
(Continued)

FOREIGN PATENT DOCUMENTS

CN 101163445 4/2008
DE 459 483 5/1928
(Continued)

OTHER PUBLICATIONS

Written Opinion of the International Searching Authority corresponding to co-pending International Patent Application No. PCT/US2006/007682, European Patent Office, dated Jul. 25, 2006, 7 pages.

(Continued)

*Primary Examiner* — Gregory Anderson
*Assistant Examiner* — Sarah Simpson
(74) *Attorney, Agent, or Firm* — Nixon Peabody LLP (57) ABSTRACT

A lancet-release mechanism is adapted to be incorporated into a lancing device. The lancing device is adapted to receive a lancet assembly therein. The lancing device is adapted to move the lancet assembly between a resting position, a cocking position, and a puncture position. The lancet-release mechanism comprises a lancet holder and a cantilever beam. The lancet holder forms a central aperture. The central aperture is adapted to receive the lancet assembly therein. The lancet holder further forms a plurality of protuberances thereon. The cantilever beam has a projection extending therefrom. The projection is adapted to engage the plurality of protuberances located on the lancet holder. The projection is adapted to separate the plurality of protuberances from each other so as to enlarge the central aperture.

6 Claims, 12 Drawing Sheets

Related U.S. Application Data (60) Provisional application No. 60/658,946, filed on Mar. 4, 2005.

(52) U.S. Cl.
CPC ...... *A61B 5/15113* (2013.01); *A61B 5/15117* (2013.01); *A61B 5/150183* (2013.01); *A61B 5/150259* (2013.01); *A61B 5/150412* (2013.01); *A61B 5/150503* (2013.01); *A61B 5/150816* (2013.01); *A61B 5/150824* (2013.01)

(58) Field of Classification Search
USPC .................................................. 606/181, 182
See application file for complete search history.

(56) References Cited

U.S. PATENT DOCUMENTS

| | | | | |
|---|---|---|---|---|
| 4,442,836 | A * | 4/1984 | Meinecke et al. | 606/182 |
| 4,449,529 | A | 5/1984 | Burns et al. | |
| 4,469,110 | A | 9/1984 | Slama et al. | |
| 4,517,978 | A | 5/1985 | Levin et al. | |
| 4,553,541 | A | 11/1985 | Burns | |
| 4,627,445 | A | 12/1986 | Garcia et al. | |
| 4,637,403 | A | 1/1987 | Garcia et al. | |
| 4,735,203 | A | 4/1988 | Ryder et al. | |
| D297,459 | S | 8/1988 | Heiland et al. | |
| 4,787,398 | A | 11/1988 | Garcia et al. | |
| RE32,922 | E | 5/1989 | Levin et al. | |
| 4,924,879 | A | 5/1990 | O'Brien | |
| 4,976,724 | A | 12/1990 | Nieto et al. | |
| 4,990,154 | A | 2/1991 | Brown et al. | |
| 5,074,872 | A | 12/1991 | Brown et al. | |
| D332,490 | S | 1/1993 | Brown et al. | |
| 5,196,025 | A | 3/1993 | Ranalletta et al. | |
| 5,231,993 | A | 8/1993 | Harber et al. | |
| 5,267,963 | A | 12/1993 | Bachynsky | |
| 5,279,294 | A | 1/1994 | Anderson et al. | |
| 5,304,193 | A | 4/1994 | Zhadanov | |
| 5,318,583 | A | 6/1994 | Rabenau et al. | |
| 5,318,584 | A * | 6/1994 | Lange et al. | 606/182 |
| 5,320,607 | A | 6/1994 | Ishibashi | |
| 5,324,303 | A | 6/1994 | Strong et al. | |
| 5,350,392 | A | 9/1994 | Purcell et al. | |
| 5,527,334 | A | 6/1996 | Kanner et al. | |
| 5,554,166 | A | 9/1996 | Lange et al. | |
| 5,575,777 | A | 11/1996 | Cover et al. | |
| 5,628,764 | A | 5/1997 | Schraga | |
| D393,716 | S | 4/1998 | Brenneman et al. | |
| D393,717 | S | 4/1998 | Brenneman et al. | |
| 5,741,288 | A | 4/1998 | Rife | |
| 5,797,942 | A | 8/1998 | Schraga | |
| 5,868,772 | A | 2/1999 | LeVaughn et al. | |
| 5,871,494 | A | 2/1999 | Simons et al. | |
| 5,916,230 | A | 6/1999 | Brenneman et al. | |
| 5,951,492 | A | 9/1999 | Douglas et al. | |
| 5,951,493 | A | 9/1999 | Douglas et al. | |
| 5,954,738 | A | 9/1999 | LeVaughn et al. | |
| 6,022,366 | A | 2/2000 | Schraga | |
| 6,045,567 | A | 4/2000 | Taylor et al. | |
| 6,048,352 | A | 4/2000 | Douglas et al. | |
| 6,050,977 | A | 4/2000 | Adams et al. | |
| 6,090,078 | A | 7/2000 | Erskine et al. | |
| 6,090,124 | A | 7/2000 | Weekes | |
| 6,093,156 | A | 7/2000 | Cunningham et al. | |
| 6,099,484 | A | 8/2000 | Douglas et al. | |
| 6,152,942 | A | 11/2000 | Brenneman et al. | |
| 6,156,051 | A | 12/2000 | Schraga et al. | |
| 6,168,606 | B1 | 1/2001 | Levin et al. | |
| 6,197,040 | B1 * | 3/2001 | LeVaughn et al. | 606/182 |
| 6,210,421 | B1 | 4/2001 | Bocker | |
| 6,231,531 | B1 | 5/2001 | Lum et al. | |
| 6,283,982 | B1 | 9/2001 | LeVaughn et al. | |
| 6,306,152 | B1 | 10/2001 | Verdonk et al. | |
| 6,322,574 | B1 | 11/2001 | Lloyd et al. | |
| 6,364,889 | B1 | 4/2002 | Kheiri et al. | |
| 6,379,317 | B1 | 4/2002 | Kintzig et al. | |
| 6,409,740 | B1 | 6/2002 | Kuhr et al. | |
| 6,419,661 | B1 | 7/2002 | Kuhr et al. | |
| 6,432,120 | B1 | 8/2002 | Teo | |
| 6,451,040 | B1 | 9/2002 | Purcell | |
| 6,514,270 | B1 | 2/2003 | Schraga | |
| 6,537,292 | B1 | 3/2003 | Lee | |
| 6,561,989 | B2 | 5/2003 | Whitson et al. | |
| 6,602,268 | B2 | 8/2003 | Kuhr et al. | |
| 6,607,543 | B2 | 8/2003 | Purcell et al. | |
| 6,749,618 | B2 | 6/2004 | LeVaughn et al. | |
| 6,752,817 | B2 | 6/2004 | Flora et al. | |
| 6,837,858 | B2 | 1/2005 | Cunningham et al. | |
| 7,144,404 | B2 | 12/2006 | Whitson | |
| 7,238,192 | B2 | 7/2007 | List et al. | |
| 7,303,573 | B2 | 12/2007 | D'Agostino | |
| 8,187,295 | B2 * | 5/2012 | Uehata | A61B 5/1411 606/182 |
| 2002/0022789 | A1 | 2/2002 | Perez et al. | |
| 2002/0029058 | A1 * | 3/2002 | Levaughn et al. | 606/181 |
| 2002/0087180 | A1 | 7/2002 | Searle et al. | |
| 2003/0171696 | A1 | 9/2003 | Dosmann | |
| 2003/0171699 | A1 | 9/2003 | Brenneman | |
| 2003/0187470 | A1 | 10/2003 | Chelak et al. | |
| 2003/0216767 | A1 | 11/2003 | List et al. | |
| 2004/0059256 | A1 | 3/2004 | Perez | |
| 2004/0248312 | A1 | 12/2004 | Vreeke et al. | |
| 2005/0085840 | A1 | 4/2005 | Yi et al. | |
| 2005/0090850 | A1 | 4/2005 | Thoes et al. | |
| 2005/0149090 | A1 | 7/2005 | Morita et al. | |
| 2005/0251188 | A1 * | 11/2005 | Chen | A61B 5/1411 606/181 |
| 2006/0229652 | A1 | 10/2006 | Iio et al. | |
| 2006/0247670 | A1 | 11/2006 | LeVaughn et al. | |
| 2008/0140105 | A1 | 6/2008 | Zhong et al. | |
| 2008/0167673 | A1 | 7/2008 | Zhong et al. | |
| 2008/0195133 | A1 | 8/2008 | Zhong et al. | |
| 2010/0179579 | A1 | 7/2010 | Purcell | |

FOREIGN PATENT DOCUMENTS

| | | | |
|---|---|---|---|
| EP | 0 115 388 A1 | 8/1984 | |
| EP | 0 204 892 A2 | 12/1986 | |
| EP | 0 569 124 A1 | 11/1993 | |
| EP | 0 894 471 A2 | 2/1999 | |
| EP | 0 898 936 A2 | 3/1999 | |
| EP | 0 958 783 A1 | 11/1999 | |
| EP | 1 535 573 A2 | 6/2005 | |
| EP | 1 541 088 A1 | 6/2005 | |
| JP | 2000175889 | 6/2000 | |
| JP | WO 2004091402 A1 * | 10/2004 | A61B 5/1411 |
| TW | 200640418 | 12/2006 | |
| WO | WO 02/100278 A1 | 12/2002 | |
| WO | WO 2004/103178 A1 | 12/2004 | |
| WO | WO 2005/001418 | 1/2005 | |
| WO | WO 2005/011496 | 2/2005 | |
| WO | WO 2005/046477 A2 | 5/2005 | |
| WO | WO 2005/077275 A1 | 8/2005 | |
| WO | WO 2006/031535 A2 | 4/2006 | |
| WO | WO 2006/096539 | 9/2006 | |
| WO | WO 2006/096540 A1 | 9/2006 | |
| WO | WO 2006/096630 A1 | 9/2006 | |
| WO | WO 2006/107914 A2 | 10/2006 | |

OTHER PUBLICATIONS

International Search Report corresponding to co-pending International Patent Application No. PCT/US2006/007682, European Patent Office, dated Jul. 25, 2006, 3 pages.

* cited by examiner

LANCET-RELEASE MECHANISM

CROSS-REFERENCE TO RELATED APPLICATIONS

This is a continuation of patent application Ser. No. 11/885,526, filed on Aug. 31, 2007, which is a National Phase Application of PCT/US2006/007682, filed on Mar. 3, 2006, which claims priority to Application No. 60/658,946 filed on Mar. 4, 2005, each of which is incorporated by reference in its entirety.

FIELD OF THE INVENTION

The present invention relates generally to diagnostic instruments and, more particularly, to a lancet-release mechanism for a lancing device.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, determining glucose in body fluids is important to diabetic individuals who must frequently check their blood glucose levels to regulate the glucose intake in their diets.

One method of obtaining a body fluid sample, such as a whole blood sample, is to use a lancing device. The whole blood sample may then be used to determine the glucose concentration of an individual. Existing lancing devices use a lancet to pierce the tissue of the skin, allowing a blood sample to form on the skin's surface. Typically, lancing devices hold the lancet within them when the lancet is not in use, so as to shield the user from injury as well as to assist in preventing or inhibiting contamination.

Existing lancing devices require two-handed operation, are dangerous, or are ineffective in releasing the lancet. Two-handed operation requires that one hand hold the lancing device while the other hand removes the lancet. This is inconvenient to many users as the lancet is small, and may cause safety problems as the lancet could pierce the user's skin inadvertently. This can cause the user pain and may also transmit diseases. Some one-handed designs eject the lancet too hard such that ejecting the lancet becomes dangerous if the lancet is not re-shielded. Still other one-handed designs do not eject the lancet effectively, as the lancet is not released from the lancet holder even after the user depresses the release mechanism. Yet other one-handed designs have complicated release mechanisms internally, such that if a user drops the lancing device, the release mechanism may jam and no longer eject the lancet from the lancing device.

It would be desirable to have a lancing device and a method for using a lancing device that addresses these issues.

SUMMARY OF THE INVENTION

According to one embodiment of the present invention, a lancet-release mechanism adapted to be incorporated into a lancing device is disclosed. The lancing device is adapted to receive a lancet assembly therein and move the lancet assembly between a resting position, a cocking position, and a puncture position. The lancet release mechanism comprises a lancet holder and a cantilever beam. The lancet holder having a central aperture adapted to receive the lancet assembly therein. The lancet holder further has a plurality of protuberances thereon. The cantilever beam has a projection extending therefrom adapted to engage the plurality of protuberances located on the lancet holder. The projection is adapted to separate the plurality of protuberances from each other so as to enlarge the central aperture.

According to another embodiment of the present invention, a release button replaces the cantilever beam of the above-described invention. The release button has a projection extending therefrom adapted to engage the plurality of protuberances located on the lancet holder. The projection is adapted to separate the plurality of protuberances from each other so as to enlarge the central aperture.

According to yet another embodiment of the present invention, a lancet-release mechanism adapted to be incorporated into a lancing device is disclosed. The lancing device is adapted to receive a lancet assembly therein and move the lancet assembly between a resting position, a cocking position, and a puncture position. The lancing device comprises a lancet holder and a first beam. The lancet holder has a central aperture adapted to receive the lancet assembly therein. The lancet holder being at least partially divided into a first portion and a second portion. The first beam is attached to the first portion of the lancet holder. The first beam has a release button located opposite the lancet holder. The first beam and release button are adapted to separate the first portion of the lancet holder from the second portion of the lancet holder when the release button is depressed. The separation of the first portion from the second portion enlarging the central aperture.

The above summary of the present invention is not intended to represent each embodiment, or every aspect, of the present invention. Additional features and benefits of the present invention are apparent from the detailed description and figures set forth below.

BRIEF DESCRIPTION OF THE DRAWINGS

FIG. 2 is a side view of the lancing device of FIG. 1a.

FIG. 8b is a perspective view of the lancet-release mechanism of FIG. 8a.

FIG. 9b is a bottom view of the lancing device of FIG. 9a.

FIG. 9c is a cross-sectional view of the lancing device of FIG. 9a.

DESCRIPTION OF ILLUSTRATED EMBODIMENTS

The present invention is directed to a lancet-release mechanism for incorporation into a stand-alone lancing device or into a lancing device that is incorporated into a meter or similar testing device. The lancing device is adapted to receive a lancet for use in drawing a body fluid from a test subject. The body fluid generally contains at least one analyte that may then be examined to determine its concentration in the body fluid sample.

Lancing devices and lancets may be used to produce a blood or body fluid sample from a test subject. This sample may then be analyzed with a meter and test strip, or similar devices, to determine the concentration of the analyte to be examined. Examples of the types of analytes that may be collected with a lancing device include glucose, lipid profiles (e.g., cholesterol, triglycerides, LDL and HDL), microalbumin, hemoglobin A1C, fructose, lactate, or bilirubin.

Figure 1A:
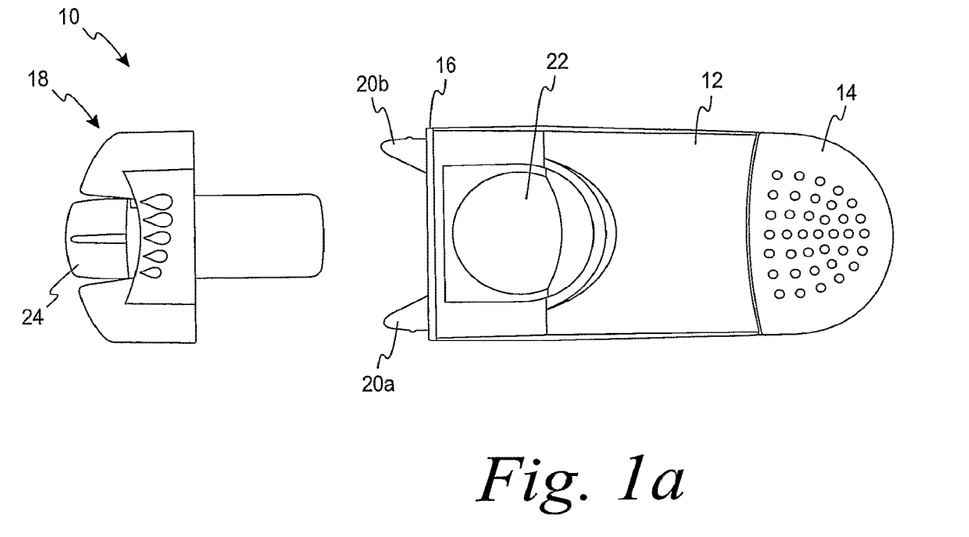
FIG. 1a is a top view of a lancing device, according to one embodiment of the present invention.
Figure 1B:
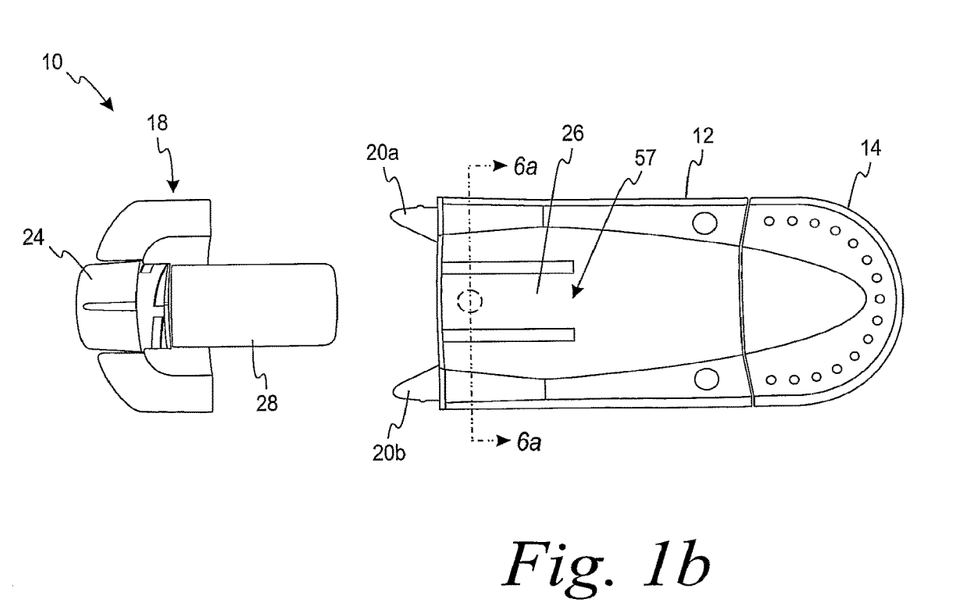
FIG. 1b is a bottom view of the lancing device of FIG. 1a, according to one embodiment of the present invention.
Figure 1C:
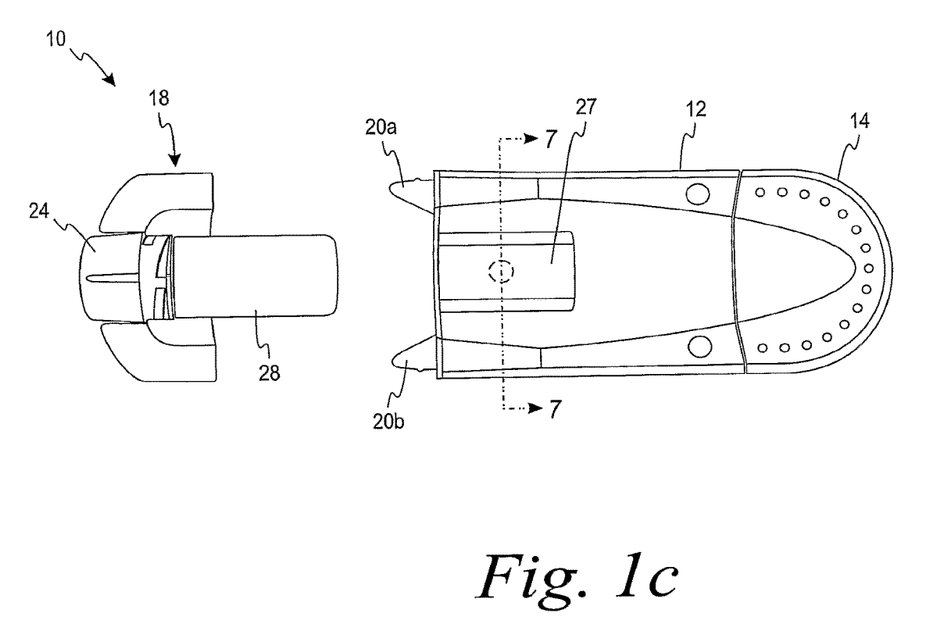
FIG. 1c is a bottom view of the lancing device of FIG. 1a, according to another embodiment of the present invention.
Figure 2:
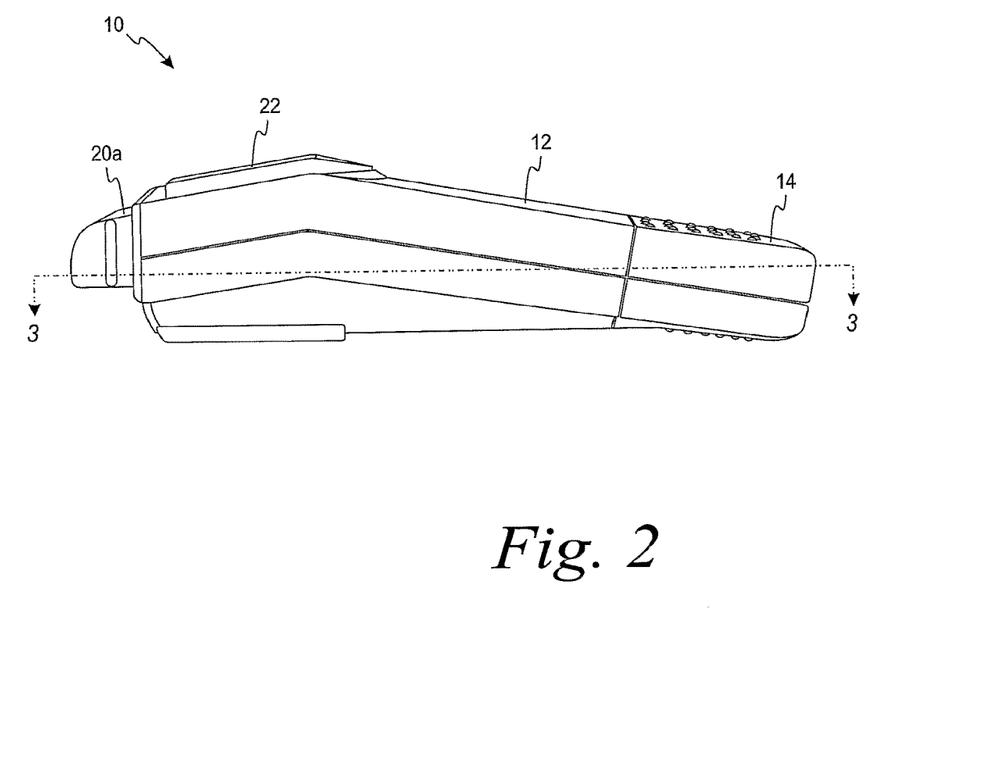

Turning now to the drawings and initially to FIGS. 1-2, a lancing device 10 for obtaining a fluid sample from a test subject is illustrated, according to one embodiment of the present invention. The lancing device 10 has a main housing 12 and a movable housing 14 that is movable relative to the main housing 12. An endcap support 16 is connected to the main housing 12 on the testing end of the lancing device 10. An endcap 18 may be removably attached to the endcap support 16. When attached, the endcap 18 is retained on the endcap support 16 by a pair of support arms 20a-b integrally formed with the endcap support 16.

According to one embodiment, the lancing device 10 also includes a cantilever beam 26 (FIG. 1b) attached to the main housing 12 near the testing end of the lancing device 10. As will be explained in greater detail with respect to FIGS. 5-6b, the cantilever beam 26 may be depressed to assist with releasing a lancet assembly from the lancing device 10. The endcap 18 is provided with an extension 28 that extends therefrom in the direction of the main housing 12 of the lancing device 10. The extension 28 helps to prevent an inadvertent depression of the cantilever beam 26 when the endcap 18 is removably attached to the endcap support 16 of the lancing device 10.

According to another embodiment of the present invention, the lancing device 10 also includes a release button 27 (FIG. 1c) located within a housing insert (not shown) formed in the main housing 12 near the testing end of the lancing device 10. A spring mechanism 94 (FIG. 7) is located between the release button 27 and the housing insert. The housing insert includes a central aperture surrounded by a shelf. The shelf is adapted to support the spring mechanism 94 and the release button 27. As will be explained in greater detail with respect to FIGS. 5 and 7, the release button may be depressed to assist with releasing a lancet assembly from the lancing device 10.

Figure 5:
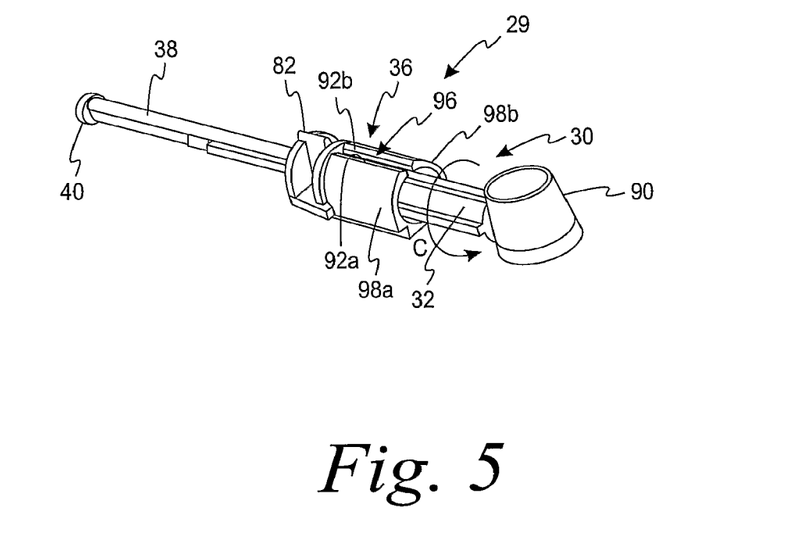
FIG. 5 is a perspective view of a lancing mechanism, according to one embodiment of the present invention.

To use the lancing device 10, the movable housing 14 is pulled away from the main housing 12 to move an internal lancing mechanism 29 (as best illustrated in FIG. 5) to a cocked position, and then a pushbutton 22 is pushed to actuate the lancing mechanism 29 so that the sharp tip of a lancet is forced through an aperture (not shown) in the endcap 18. The lancing device 10 may be provided with a number of different endcaps 18, each having a different width, to facilitate the formation of skin punctures of various depths. Alternatively, the endcap 18 may include an adjustable dial 24 for allowing punctures of different depths to be performed utilizing a single endcap 18.

Figure 3:
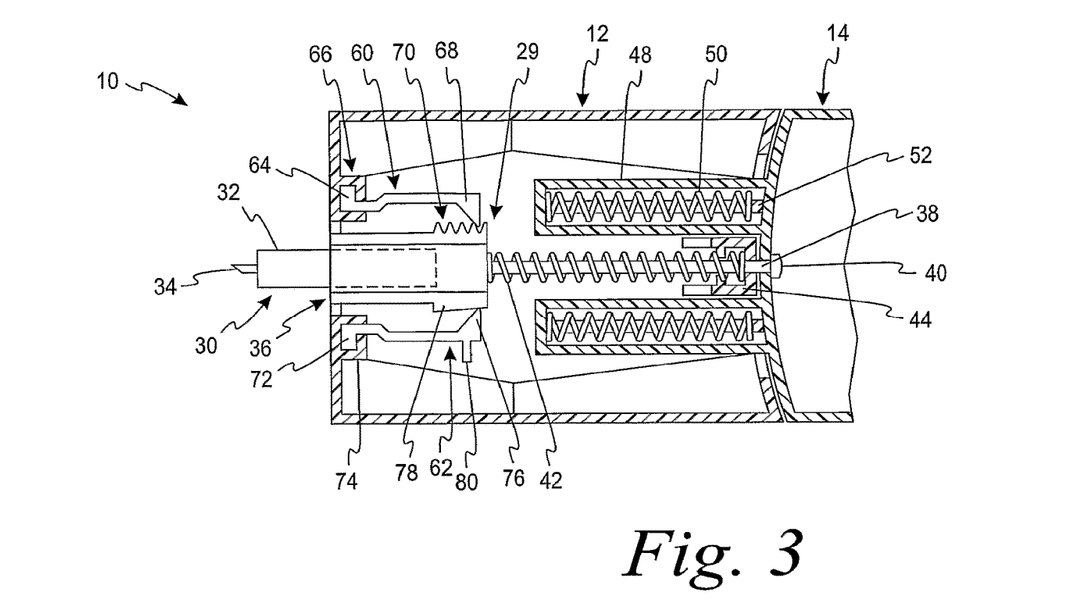
FIG. 3 is a cross-sectional, top view of the lancing device of FIG. 2 in a resting position.

Turning now to FIG. 3, a cross-sectional view of a portion of the lancing device 10 is illustrated with the endcap 18 and endcap support 16 not shown. A lancet assembly 30 having a lancet body 32 and a lance 34 is received within an internal cylindrical aperture 58 (FIGS. 6-7) formed in a generally cup-shaped lancet holder 36. The lancet holder 36 is connected to an elongated shaft 38 by being integrally formed therewith. The shaft 38 has an enlarged end 40 that is supported within the movable housing 14. A drive spring 42 is disposed around the shaft 38 between the lancet holder 36 and a spring stop 44 (see also FIG. 4) integrally formed with the main housing 12.

The movable housing 14 has a pair of elongate spring trays 48 integrally formed therewith. A return spring 50 is disposed within each of the spring trays 48, a first end of each return spring 50 being disposed against an internal surface of the spring tray 48 and a second end of each return spring 50 being disposed against a spring stop 52 integrally formed with the main housing 12. The spring stops 52 extend into the spring trays 48 through an elongate slot 54 (see FIG. 4) formed in the bottom portion of each tray 48.

A damping arm 60 and a retaining arm 62 are disposed adjacent opposite sides of the lancet holder 36. The damping arm 60 has a first end 64 that is held within a retaining structure 66 integrally formed with the main housing 12. A second pointed end 68 of the damping arm 60 is disposed adjacent a corrugated surface 70 formed on an outside portion of the lancet holder 36. The retaining arm 62 has a first end 72 that is held within a retaining structure 74 integrally formed with the main housing 12. A second pointed end 76 of the retaining arm 62 is disposed adjacent an angled stop member 78. The lower side of the retaining arm 62 rests on a support member 80. The arms 60, 62 are biased inwardly towards the lancet holder 36 so that they make contact with the respective outer sides of the lancet holder 36.

Figure 4:
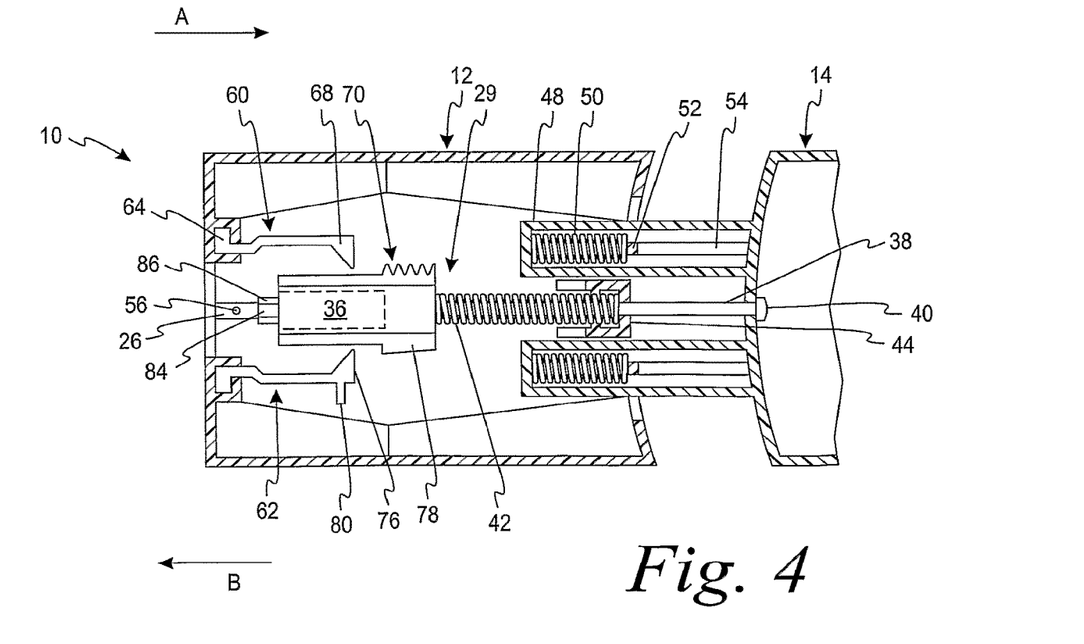
FIG. 4 is a cross-sectional, top view of the lancing device of FIG. 2 in a cocking position.

FIG. 3 illustrates the interior of the lancing device 10 when the lancing device 10 is not in use. In this position, the lancet holder 36 is disposed in a resting position between a puncture position and a cocked position. FIG. 4 illustrates the interior of the lancing device 10 (the lancet assembly 30 is not shown) when the lancet holder 36 is in a cocked position in which the movable housing 14 has been pulled away from the main housing 12.

Referring to FIG. 4, to move the lancet holder 36 from its resting position to its cocked position, the movable housing 14 is pulled away from the main housing 12 in the direction of Arrow A. The movable housing 14 continues to be pulled against the force of the drive spring 42—until the angled stop member 78 formed on the lancet holder 36 moves past (to the right of as illustrated in FIG. 4) the pointed end 76 of the retaining arm 62. At that point, the bias of the retaining arm 62 will force its pointed end 76 inwardly, so that the pointed end 76 makes contact with the side of the lancet holder 36 disposed on the testing end side of the angled stop member 78. When in that cocked position, movement of the lancet holder 36 in the direction of Arrow B due to the drive spring 42 is prevented because of the contact between the pointed end 76 of the retaining aim 62 and the angled stop member 78. After the lancet holder 36 is placed in the cocked position, the user allows the return springs 50 to force the movable housing 14 back to its initial position adjacent the main housing 12.

The lancet holder 36 is guided between its resting and cocked positions by a guide rib 82 (FIG. 5) formed on the bottom portion of the lancet holder 36 that rides within a groove 84 formed between a pair of raised guide rails 86 formed in a bottom interior portion of the main housing 12.

To perform a puncture on a test subject's skin, the endcap 18 is attached to the lancing device 10. The lancet holder 36 may be in the cocked position at the time the endcap 18 is attached or may be cocked once the endcap 18 is in position. The endcap 18 is then placed firmly against the skin where the puncture is to be made, and the pushbutton 22 is depressed. Depressing the pushbutton 22 causes an angled release arm (not shown), integrally formed with the bottom of the pushbutton 22 and which passes through an aperture (not shown) in the main housing 12, to force the retaining aim 62 away from the lancet holder 36. Thus, the lancet holder 36 is no longer prevented from moving in the direction of Arrow B by the contact of the angled stop member 78 with the pointed end 76 of the retaining arm 62. A spring mechanism—for example, an elastically deformable foam material—may be disposed between the pushbutton 22 and a portion of the main housing 12 to bias the pushbutton 22 to its non-actuated position.

Upon release of the lancet holder 36 as described above, the drive spring 42 will force the lancet holder 36 in the direction of Arrow B until the sharp point of the lance 34 (FIG. 3) passes through the aperture (not shown) in the endcap 18 to make the puncture. When the puncture is made, the drive spring 42 will be in a stretched position, and after the puncture is made the contraction of the drive spring 42 will draw the lancet holder 36 back towards its resting position shown in FIG. 3.

As the lancet holder 36 moves from its puncture position back to its resting position shown in FIG. 3, the pointed tip 68 of the damping arm 60 will make frictional contact with the corrugated surface 70. This frictional contact decelerates or dampens the movement of the lancet holder 36. Such damping assists in preventing or inhibiting the drive spring 42—and its natural tendency to oscillate (due to its being elastically deformable)—from causing a second, unintended skin puncture to be made. As used herein, the term "corrugated" refers to a surface having raised ribs or other structures, either regularly or irregularly spaced, for providing an increased amount of friction when the surface is brought into contact with a damping member.

Figure 6A:
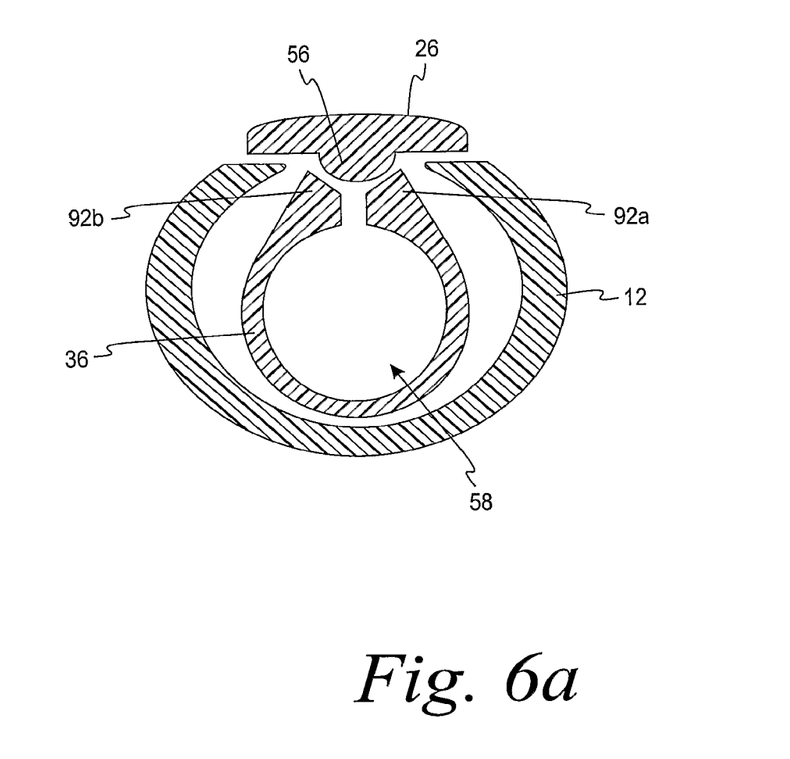
FIG. 6a is a cross-sectional view of the lancing device of FIG. 1b, according to one embodiment of the present invention.
Figure 6B:
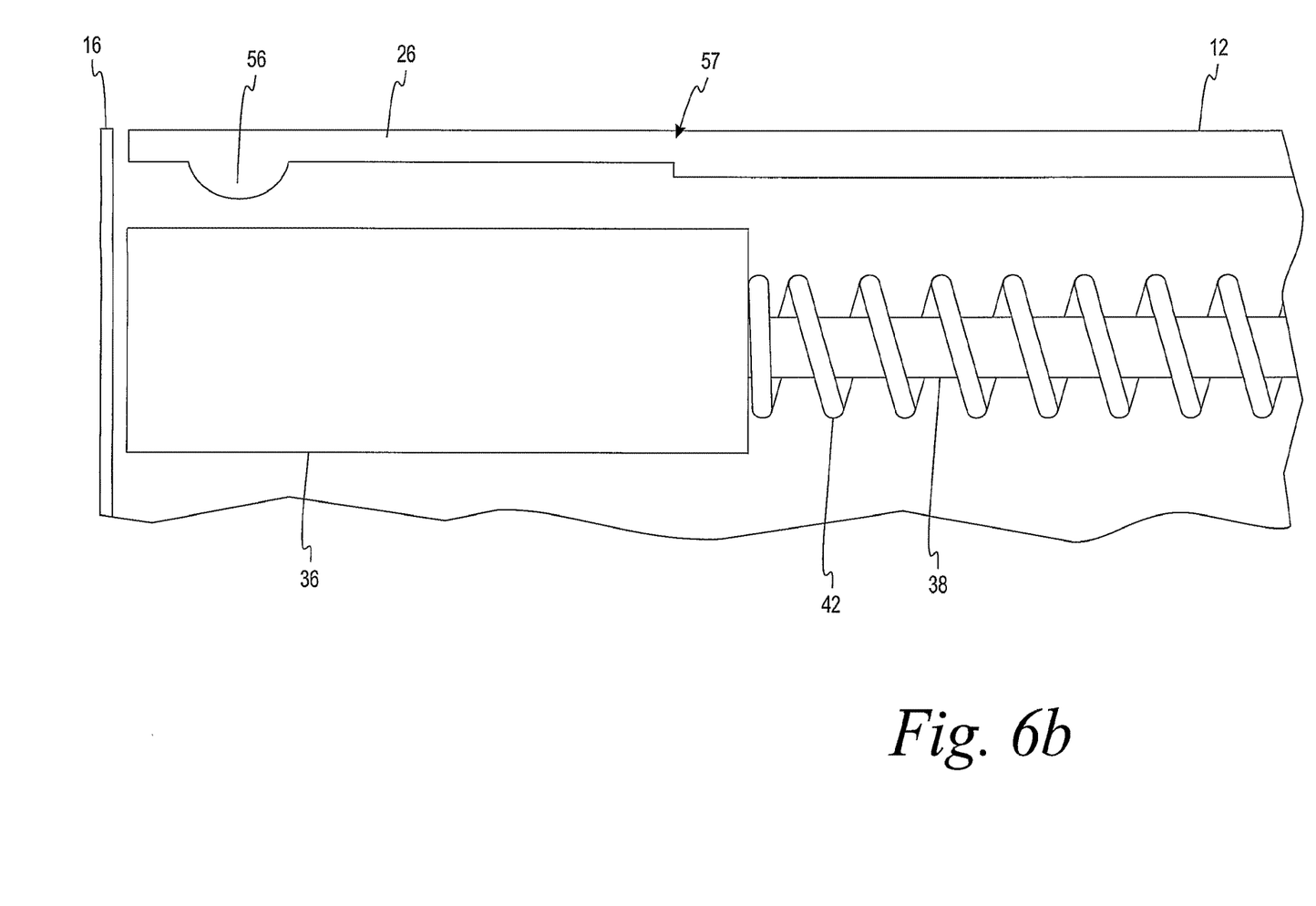
FIG. 6b is a partial-side view of a portion of the lancing mechanism of FIG. 5 and cantilever beam, according to one embodiment of the present invention.

The cantilever beam 26 (or release button 27, illustrated in FIG. 7) includes a projection 56 extending therefrom through the main housing 12. The projection 56 is adapted to engage the lancet holder 36. As discussed above, the cantilever beam 26 and release button 27 are depressible by a user from outside the main housing 12 to release the lancet assembly 30 from the lancet holder 36. Depression by a user of the cantilever beam 26 or release button 27 causes the projection 56 to engage the lancet holder 36, as will be explained in greater detail with respect to FIGS. 6-7.

Turning now to FIG. 5, a perspective view of the lancing mechanism 29 is illustrated, according to one embodiment of the present invention. The lancet mechanism 29 includes the lancet holder 36 adapted to receive the lancet assembly 30. As illustrated in FIG. 5, the lancet assembly 30 is disposed within the generally cylindrical aperture formed in the lancet holder 36. The lancet assembly 30 is shown with a protective cap 90 that has a portion that is integrally formed with the lancet body 32 and which covers the sharp point of the lance 34. Prior to using the lancing device 10, the lancet body 32 of a new lancet assembly 30 is inserted into the cylindrical aperture disposed in the lancet holder 36, and then the protective cap 90 is twisted off of the lancet assembly 30, in the direction of the Arrow C shown in FIG. 5.

The lancet holder 36 includes a plurality of protuberances 92a,b that extend therefrom. The protuberances 92a,b are located proximate the edges of a gap 96 that is located between a first portion 98a and a second portion 98b of the lancet holder 36. In one embodiment, the protuberances 92a,b are formed by a buildup of material added during the molding process. The protuberances 92a,b are attached to, or formed on, the lancet holder 36 such that, when the cantilever beam 26 (FIG. 1b), or release button 27 (FIG. 1c), is depressed, the projection 56 of the cantilever beam 26 or release button 27 engages the protuberances 92a,b. The engagement by the projection 56 forces the first and second portions 98a,b of the lancet holder 36 apart, causing the internal cylindrical aperture of the lancet holder 36 to expand. The expansion of the lancet holder 36 allows the lancet assembly 30 to freely release from the lancet holder 36.

Referring also to FIG. 6a, a cross-sectional view of the lancing device 10 is illustrated, according to one embodiment. As illustrated, the projection 56 of the cantilever beam 26 is centered between the protuberances 92a,b of the lancet holder 36. When the cantilever beam 26 is depressed in the direction of the lancet holder 36, the projection 56 engages the protuberances 92a,b. As the cantilever beam 26 continues to be depressed, the projection 56 forces the protuberances 92a,b apart, thus causing the aperture 58 to enlarge and the lancet holder 36 to expand. As the aperture 58 becomes larger, the lancet assembly 30 disengages from the lancet holder 36 and is easily removed from the lancet holder 36 via a user or gravity.

Referring also to FIG. 6b, a partial-side view of a portion of the lancing mechanism 29 (FIG. 5) and cantilever beam 26 are illustrated, according to one embodiment. The cantilever beam 26 is integrally formed with the main housing 12 and may be formed, for example, by laser cutting the main housing 12 to free the cantilever beam 26 (as best illustrated in FIG. 1c). The cantilever beam 26 is adapted to flex at a pivot 57 when a user depresses the cantilever beam 26 in the direction of the lancet holder 36. This depression—and the subsequent flexing—causes the projection 56 to engage the lancet holder 36 as described above with respect to FIG. 6a.

Figure 7:
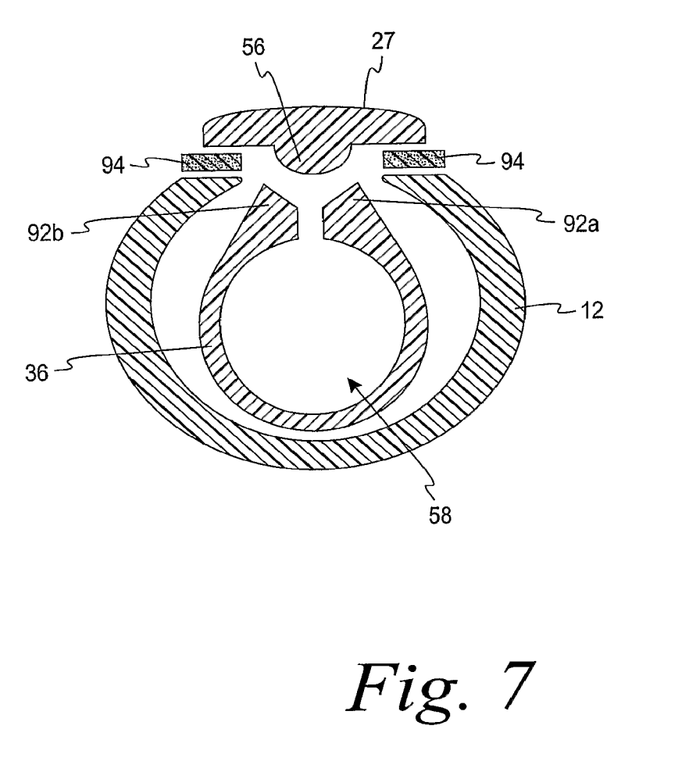
FIG. 7 is a cross-sectional view of the lancing device of FIG. 1c, according to yet another embodiment of the present invention.

Turning now to FIG. 7, a cross-sectional view of the lancing device 10 is illustrated, according to another embodiment of the present invention. The lancing device 10 includes the release button 27 and the spring mechanism 94 disposed between the release button 27 and the main housing 12. The release button 27 is distinct from the main housing 12 and is free floating within a housing insert (not shown). The spring mechanism 94 is used to bias the free-floating release button 27 away from the protuberances 92a,b of the lancet holder 36 to assist in preventing or inhibiting accidental engagement by the projection 56 formed on the release button 27. When the release button 27 is depressed by a user towards the lancet holder 36, the entire release button 27 depresses—compressing the spring mechanism 94—and causes the projection 56 to engage the protuberances 92a-b. The spring mechanism may be, for example, a deformable foam material or other suitable material sufficient to bias the release button 27 away from the lancet holder 36.

Figure 8A:
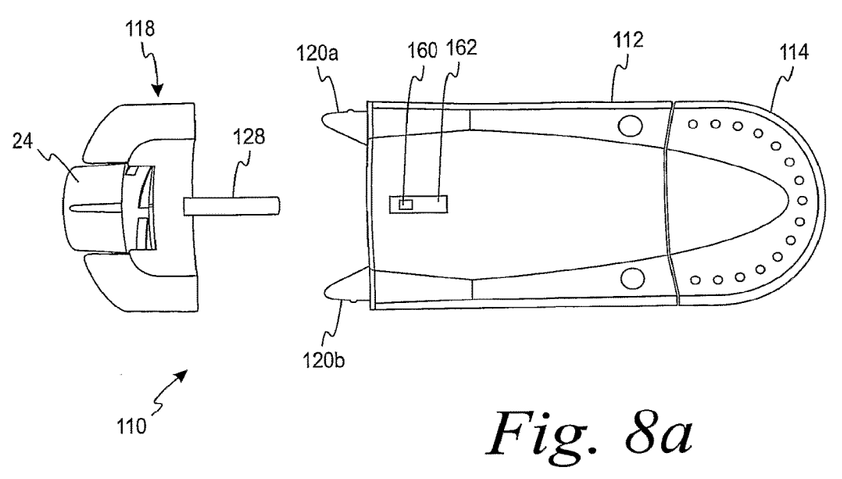
FIG. 8a is a bottom view of a lancing device including a lancet-release mechanism, according to one embodiment of the present invention.
Figure 8B:
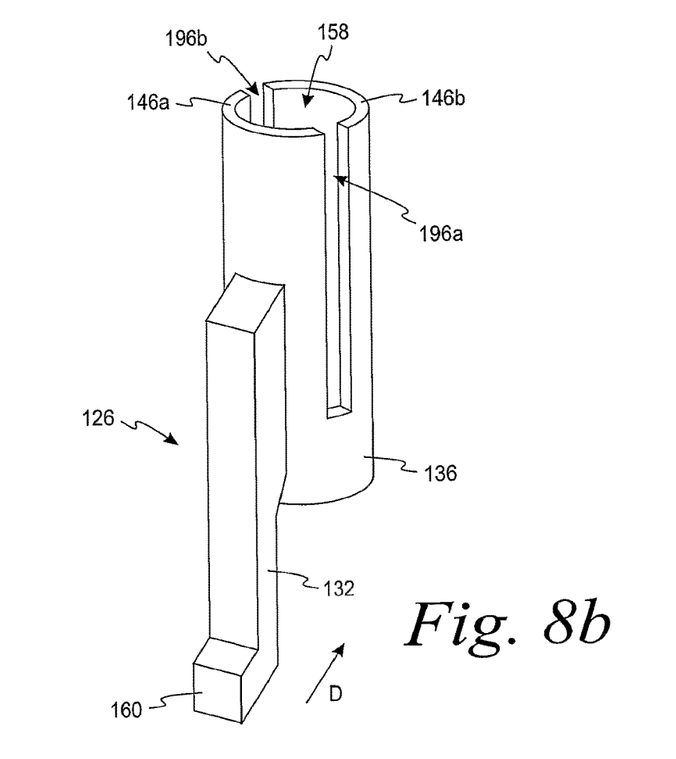

Turning now to FIGS. 8a-b, a lancing device 110 is illustrated according to yet another embodiment of the present invention. The lancing device 110 includes a movable housing portion 114 and a main housing portion 112. The main housing 112 includes a pair of support arms 120a,b for removably attaching an endcap 118 thereto. The endcap 118 includes an extension 128 that assists in preventing a lancet release device from being inadvertently depressed.

A release button 160 extends through an aperture 162 formed in the main housing 112. The release button 160 is allowed to slide within the aperture 162 as the lancing device 110 is moved between a resting position, a cocked position, and a firing position. The release button 160 is included in a lancet-release mechanism 126 and extends from a beam 132 attached to a lancet holder 136. The lancet holder 136 includes a first portion 146a and a second portion 146b partially separated by a plurality of gaps 196a,b. The lancet holder 126 forms a central aperture 158 adapted to receive the lancet assembly 30. The lancet-release mechanism 126 is attached to the first portion 146a of the lancet holder 136, opposite the release button.

To release a lancet assembly 30 from the lancet holder 136 once it has been received, the release button 160 is depressed in the direction of the main housing 112 (illustrated by Arrow D in FIG. 8b) towards the longitudinal axis of the lancet holder 136. The depression of the release button 160 causes the lancet-release mechanism 126 to separate the first portion 146a of the lancet holder 136 from the second portion 146b. This separation enlarges the central aperture 158 and thus, assists in releasing the lancet assembly 30 from the lancet holder 136.

Figure 9A:
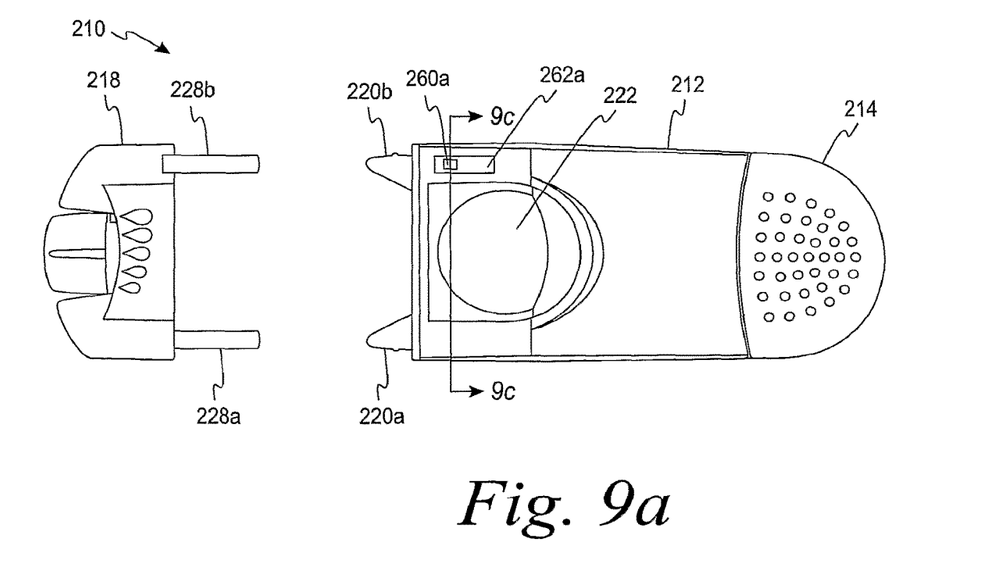
FIG. 9a is a top view of a lancing device including a lancet-release mechanism, according to yet another embodiment of the present invention.
Figure 9B:
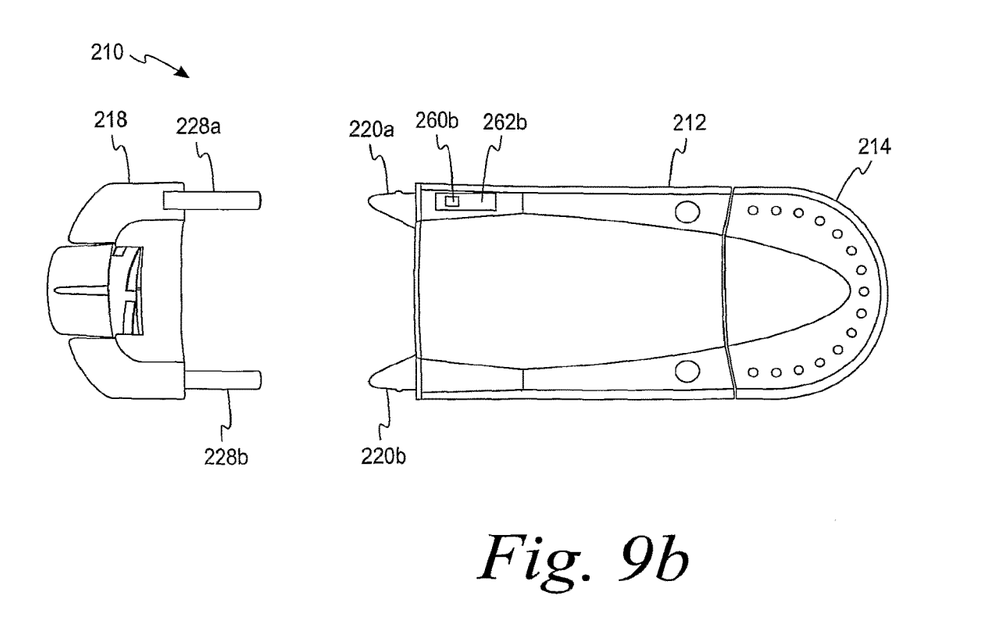
Figure 9C:
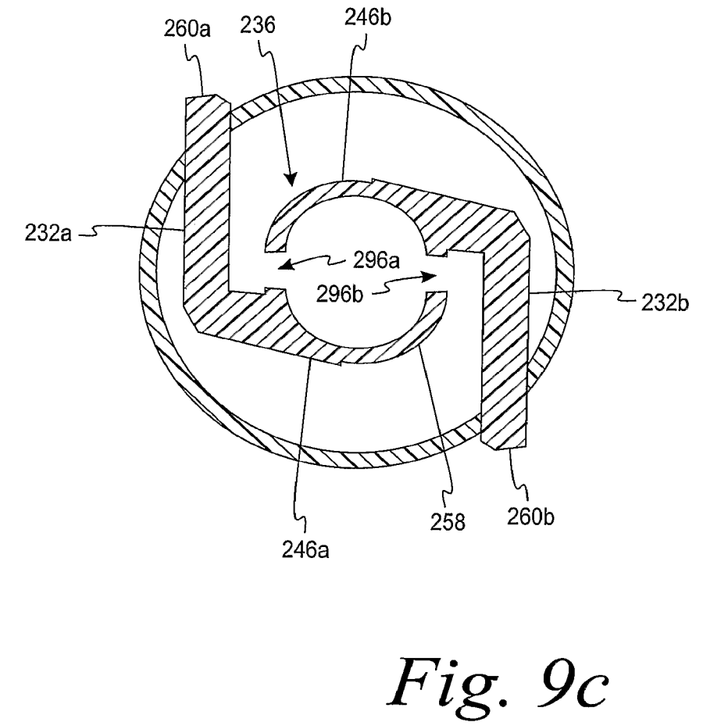

Turning now to FIGS. 9a-c, a lancing device 210 is illustrated according to yet another embodiment of the present invention. The lancing device 210 includes a movable housing portion 214 and a main housing portion 212. The main housing 212 includes a pair of support aims 220a,b for removably attaching an endcap 224 thereto. An endcap 218 includes a plurality of extensions 228a,b that assists in preventing or inhibiting a plurality of release buttons 260a,b from being inadvertently depressed.

The plurality of release buttons 260a,b extends through a respective aperture 262a,b formed in the main housing 212. The release buttons 260a,b are allowed to slide within the apertures 262a,b as the lancing device 210 is moved between a resting position, a cocked position, and a firing position. The release buttons 260a,b are included in a lancet-release mechanism and each extend from a respective beam 232a,b attached to a lancet holder 236. The lancet holder 236 includes a first portion 246a and a second portion 246b partially separated by a plurality of gaps 296a,b. The lancet holder 226 forms a central aperture 258 adapted to receive the lancet assembly 30. The beam 232a is attached to the first portion 246a of the lancet holder 236, opposite the release button, while the beam 232b is similarly attached to the second portion 246b.

To release a lancet assembly 30 from the lancet holder 236 once it has been received, the release buttons 260a,b are depressed in the direction of the main housing 212 (illustrated by Arrows E in FIG. 9c), substantially perpendicular to the longitudinal axis of the lancet holder 236 (though the depression of the release buttons 260a,b may cause a slight rotation of the beams 232a,b around the longitudinal axis). The depression of the release button 260a,b causes the lancet-release mechanism to separate the first portion 246a of the lancet holder 236 from the second portion 246b. This separation enlarges the central aperture 258 and thus, assists in releasing the lancet assembly 30 from the lancet holder 236.

Figure 10A:
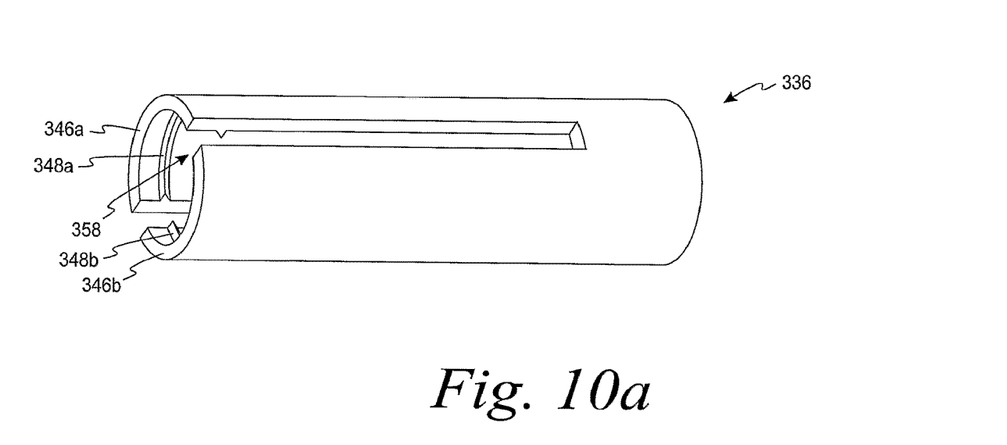
FIG. 10a is a perspective view of a lancet holder, according to one embodiment of the present invention.
Figure 10B:
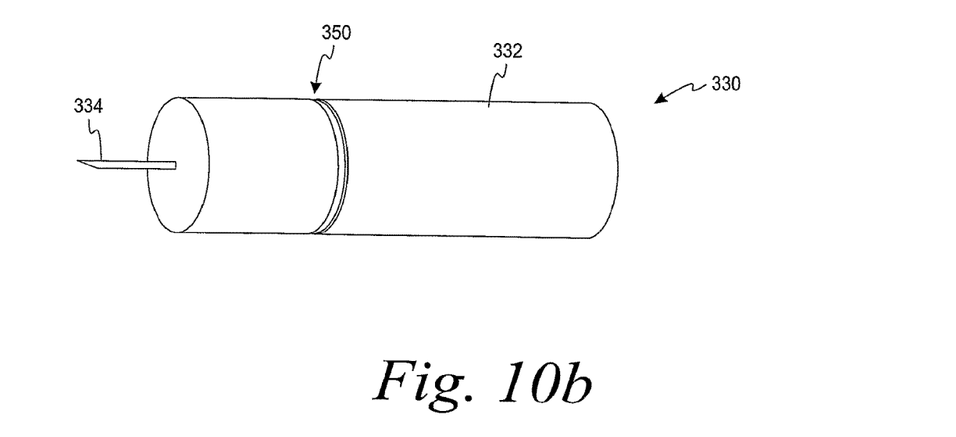
FIG. 10b is a perspective view of a lancet assembly adapted to be received by the lancet holder of FIG. 10a, according to one embodiment of the present invention.

Turning now to FIGS. 10a-b, a lancet holder 336 and a lancet assembly 330 are illustrated, according to yet another embodiment of the present invention. The lancet holder 336 is illustrated as having a first portion 346a and a second portion 348b, though it should be apparent to one skilled in the art that the lancet holder 336 may have a single portion such as illustrated in FIGS. 5-7. Each portion 346a,b of the lancet holder 336 includes a respective ridge 348a,b. The ridges 348a,b are adapted to be received within a groove 350 formed on a lancet body 332 of the lancet assembly 330 once the lancet assembly 330 is received within a central aperture 358 of the lancet holder 336. A lance 334 adapted to pierce the skin of a test subject extends from the lancet body 332.

The groove 350 and the ridges 348a,b can be triangular in shape, as illustrated, or may be any other complimentary or similar shapes so as to engage each other. According to one embodiment of the present invention, a groove is formed in the lancet holder while a corresponding ridge is formed on the lancet assembly.

By utilizing the ridges 348a,b to engage the groove 350, the frictional contact required between the lancet assembly 330 and the lancet holder 336 can be reduced or increased. Where the frictional contact is reduced, the enlargement of the central aperture 358 necessary to freely release the lancet assembly 330 can be reduced. As should be understood from the above, the lancet holder 336 and lancet assembly 330 can be utilized individually within a lancing device or may be used in conjunction with the above disclosed release mechanisms or any other type of lancet release mechanism.

Alternative Embodiment A

A lancet-release mechanism adapted to be incorporated into a lancing device, the lancing device being adapted to receive a lancet assembly therein, the lancing device being adapted to move the lancet assembly between a resting position, a cocking position, and a puncture position, the lancet release mechanism comprising:

a lancet holder having a central aperture, the central aperture being adapted to receive the lancet assembly therein, the lancet holder further having a plurality of protuberances thereon; and a cantilever beam having a projection extending therefrom, the projection being adapted to engage the plurality of protuberances located on the lancet holder, the projection being adapted to separate the plurality of protuberances from each other so as to enlarge the central aperture.

Alternative Embodiment B

The lancet-release mechanism of Alternative Embodiment A wherein the lancing device is adapted to removably attach to an endcap.

Alternative Embodiment C

The lancet-release mechanism of Alternative Embodiment B wherein the endcap includes an extension adapted to assist in inhibiting an inadvertent depression of the cantilever beam.

Alternative Embodiment D

The lancet-release mechanism of Alternative Embodiment A wherein the lancet holder includes a ridge adapted to engage a groove located on the lancet assembly.

Alternative Embodiment E

A lancet-release mechanism adapted to be incorporated into a lancing device, the lancing device adapted to receive a lancet assembly therein, the lancing device being adapted to move the lancet assembly between a resting position, a cocking position, and a puncture position, the lancing device comprising:

a lancet holder having a central aperture, the central aperture being adapted to receive the lancet assembly therein, the lancet holder being at least partially divided into a first portion and a second portion; and a first beam attached to the first portion of the lancet holder, the first beam having a release button located opposite the lancet holder, the first beam and release button being adapted to separate the first portion of the lancet holder from the second portion of the lancet holder when the release button is depressed, the separation of the first portion from the second portion enlarging the central aperture.

Alternative Embodiment F

The lancet-release mechanism of Alternative Embodiment E wherein depressing the release button in a direction of a longitudinal axis of the lancet holder causes the first portion of the lancet holder to separate from the second portion.

Alternative Embodiment G

The lancet-release mechanism of Alternative Embodiment E further comprising a second beam, the second beam having a release button located opposite the lancet holder, the second beam being attached to the second portion of the lancet holder, the second beam and release button being adapted to separate the second portion of the lancet holder from the first portion of the lancet holder when the release button is depressed.

Alternative Embodiment H

The lancet-release mechanism of Alternative Embodiment G wherein depressing the release buttons in a direction substantially perpendicular to a longitudinal axis of the lancet holder causes the first and second portions of the lancet holder to separate.

Alternative Embodiment I

The lancet-release mechanism of Alternative Embodiment E wherein the release button is externally accessible from the lancing device.

Alternative Embodiment J

The lancet-release mechanism of Alternative Embodiment E wherein the lancet holder includes a ridge adapted to engage a groove located on the lancet assembly.

Alternative Embodiment K

A lancet-release mechanism adapted to be incorporated into a lancing device, the lancing device being adapted to receive a lancet assembly therein, the lancing device being adapted to move the lancet assembly between a resting position, a cocking position, and a puncture position, the lancet release mechanism comprising:

a lancet holder having a central aperture, the central aperture being adapted to receive the lancet assembly therein, the lancet holder further having a plurality of protuberances thereon; and a release button having a projection extending therefrom, the projection being adapted to engage the plurality of protuberances located on the lancet holder, the projection being adapted to separate the plurality of protuberances from each other so as to enlarge the central aperture.

Alternative Embodiment L

The lancet-release mechanism of Alternative Embodiment K further comprising a spring mechanism located between at least of portion of the release button and the lancing device.

Alternative Embodiment M

The lancet-release mechanism of Alternative Embodiment L wherein the spring mechanism is an elastically deformable foam material.

Alternative Embodiment N

The lancet-release mechanism of Alternative Embodiment K wherein the release button is distinct from a main housing of the lancing device.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention as defined by the appended claims.

The invention claimed is:

1. A lancet-release mechanism configured to be incorporated into a lancing device, the lancing device configured to receive a lancet assembly therein, the lancing device being configured to move the lancet assembly between a resting position, a cocking position, and a puncture position, the lancet-release mechanism comprising:

a lancet holder including a central aperture, the central aperture being configured to receive the lancet assembly therein, the lancet holder having a first end and a second end opposite the first end, the first end of the lancet holder including a first portion and a second portion, the first and second portions being divided by a plurality of gaps, the second end of the lancet holder being formed in the absence of the plurality of gaps;

a first beam having a first end and a second opposing end, the first end of the first beam being attached to the first portion of the lancet holder;

a first release button extending from the second opposing end of the first beam;

a second beam having a third end and a fourth opposing end, the third end of the second beam being attached to the second portion of the lancet holder; and a second release button extending from the fourth opposing end of the second beam, wherein, in response to the first release button being depressed, the first beam is configured to separate the first portion of the lancet holder from the second portion of the lancet holder, thereby enlarging the first end of the lancet holder without enlarging the second end of the lancet holder, wherein, in response to the second release button being depressed, the second beam is configured to separate the second portion of the lancet holder from the first portion of the lancet holder, thereby enlarging the first end of the lancet holder without enlarging the second end of the lancet holder, wherein, in response to the first release button and the second release button being depressed simultaneously, the first portion of the lancet holder and the second portion of the lancet holder separate, thereby enlarging the first end of the central aperture without enlarging the second end of the central aperture.

2. The lancet-release mechanism of claim 1, wherein the first beam and the second beam extend in opposite directions generally perpendicular to a plane passing through a longitudinal axis of the lancet holder.

3. The lancet-release mechanism of claim 1, wherein the plurality of gaps includes a first gap and a second gap and each gap is generally parallel to a longitudinal axis of the lancet holder.

4. The lancet-release mechanism of claim 3, wherein the first beam is adjacent to the first gap and opposing the second gap, and wherein the second beam is adjacent to the second gap and opposing the first gap.

5. The lancet-release mechanism of claim 1, wherein the first release button and the second release button are externally accessible from the lancing device.

6. The lancet-release mechanism of claim 1, wherein the lancet holder includes a ridge configured to engage a groove located on the lancet assembly.

\* \* \* \* \*